12) United States Patent
Bratkovski et al.

(10) Patent No.: US 7,733,481 B1
(45) Date of Patent: Jun. 8, 2010

(54) FACILITATING SURFACE ENHANCED RAMAN SPECTROSCOPY

(75) Inventors: Alexandre Bratkovski, Mountain View, CA (US); Zhaoning Yu, Mountain View, CA (US); Ekaterina Ponizovskaya, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 329 days.

(21) Appl. No.: 11/980,180

(22) Filed: Oct. 30, 2007

(51) Int. Cl.
*G01J 3/44* (2006.01)
(52) U.S. Cl. .................................. 356/301
(58) Field of Classification Search ............. 356/301, 356/244, 246
See application file for complete search history.

(56) References Cited

U.S. PATENT DOCUMENTS

2006/0119853 A1* 6/2006 Baumberg et al. .......... 356/445
2007/0215843 A1 9/2007 Soukoulis et al.

FOREIGN PATENT DOCUMENTS

WO WO 2006/023195 A2 3/2006

OTHER PUBLICATIONS

Perney, N., et. al., "Tuning Localized Plasmons In Nanostructured Substrates For Surface-Enhanced Raman Scattering," Optics Express 14(2), 847-857 (Jan. 23, 2006).
Yu, Z., et. al., "Fabrication Of Large Area Subwavelength Antirefection Structures On Si Using Trilayer Resist . . . ," J. Vac. Sci. Technol. B 21(6), 2874-77 (Nov./Dec. 2003).
Li, W., et. al., Sacrificial Polymers For Nanofluidic Channels In Biological Applications, Nanotechnology 14, 1-6 (2003).
Dolling, G., et. al., "Low-Loss Negative-Index Metamaterial At Telecommunication Wavelengths," Optics Letters 31(12) 1800-1802 (Jun. 15, 2006).
Dolling, G., et. al., "Negative-Index Metamaterial At 780 nm Wavelength," Optics Letters 32(1) 53-55 (Jan. 1, 2007).

* cited by examiner

*Primary Examiner*—Tarifur Chowdhury
*Assistant Examiner*—Abdullahi Nur (57) ABSTRACT

An apparatus and related methods for facilitating surface-enhanced Raman spectroscopy (SERS) are described along with methods for fabricating the apparatus. For one embodiment, the apparatus comprises a metallic fishnet defining a plurality of voids therein. The metallic fishnet exhibits at least one acute V-shaped cross-sectional feature between at least one adjacent pair of the voids.

16 Claims, 7 Drawing Sheets

FACILITATING SURFACE ENHANCED RAMAN SPECTROSCOPY

FIELD

This patent specification relates to Raman spectroscopy. More particularly, this patent specification relates to Surface Enhanced Raman Spectroscopy (SERS) in which SERS-active structures are used to intensify Raman signals from analyte molecules disposed adjacent thereto or adsorbed thereonto.

BACKGROUND

Raman spectroscopy is a technique for performing chemical analysis. High intensity monochromatic light, such as that provided by a laser, is directed onto an analyte molecule (or sample) that is to be chemically analyzed. A majority of the incident photons are elastically scattered by the analyte molecule, wherein the scattered photons have the same energy (and, therefore, the same frequency) as the incident photons. This elastic scattering is termed Rayleigh scattering, and the elastically scattered photons and radiation are termed Rayleigh photons and Rayleigh radiation, respectively. However, a small fraction of the photons (e.g., about 1 in $10^7$ photons) are inelastically scattered by the analyte molecules. These inelastically scattered photons have a different frequency than the incident photons. This inelastic scattering of photons is termed the Raman effect. The inelastically scattered photons may have frequencies greater than, or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the Stokes radiation. A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the anti-Stokes radiation.

The Stokes and the anti-Stokes radiation is detected by a detector, such as a photomultiplier or a wavelength-dispersive spectrometer, which converts the energy of the impinging photons into an electrical signal. The characteristics of the electrical signal are at least partially a function of the energy (or wavelength, frequency, wave number, etc.) of the impinging photons and the number of the impinging photons per unit time (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against their frequency or, equivalently and more commonly, their wavenumber in units of inverse centimeters. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to non-SERS Raman spectroscopy for a sample with the same number of analyte molecules. In SERS, the analyte molecules are adsorbed onto, or placed adjacent to, an activated metal surface or structure, termed herein a SERS-active structure. The interactions between the molecules and the SERS-active structure cause an increase in the strength of the Raman signal.

Several SERS-active structures have been employed in SERS techniques, including activated electrodes in electrolytic cells, activated metal colloid solutions, and activated metal substrates such as a roughened metal surface or metal islands formed on a substrate. For example, it has been observed that adsorbing analyte molecules onto or near a specially roughened metal surface made from silver or gold may enhance the Raman scattering intensity by factors of between $10^3$ and $10^6$. SERS active structures providing greater amounts of Raman intensification would promote increased precision in SERS-based molecular sensing, and would also promote progress toward other practical goals such as reduced size, reduced complexity, reduced cost, and increased flexibility of SERS devices. Other issues arise as would be apparent to one skilled in the art upon reading the present disclosure.

SUMMARY

In one embodiment, an apparatus for facilitating surface-enhanced Raman spectroscopy (SERS) is provided, comprising a metallic fishnet defining a plurality of voids therein. The metallic fishnet exhibits at least one acute V-shaped cross-sectional feature between at least one adjacent pair of the voids.

Also provided is a method for fabricating a SERS-active structure. The method comprises forming a metallic fishnet having a predetermined lateral metallic conductor pattern that defines a corresponding predetermined lateral void pattern. To form the metallic fishnet, a plurality of vertically extending islands of shadow-masking material are laterally patterned on a substrate according to the predetermined lateral void pattern, and a metal is shadow-deposited on the substrate to form a plurality of metallic conductors thereon according to the predetermined lateral metallic conductor pattern. The vertically extending islands of shadow-masking material are configured and dimensioned such that each of the shadow-deposited metallic conductors exhibits at least one acute V-shaped cross-sectional feature extending outward from the substrate.

Also provided is a method for SERS, comprising causing at least one analyte molecule to be disposed near a metallic fishnet, the metallic fishnet defining a plurality of voids therein and exhibiting at least one acute V-shaped cross-sectional feature between at least one adjacent pair of the voids. The method further comprises causing incident electromagnetic radiation to impinge upon the at least one analyte molecule disposed near the metallic fishnet, and causing Raman radiation scattered from the at least one analyte molecule to be detected.

BRIEF DESCRIPTION OF THE DRAWINGS

FIG. 8A illustrates a side view of the SERS-active structure of FIG. 8A and a corresponding electric field map.

DETAILED DESCRIPTION

Figure 1:
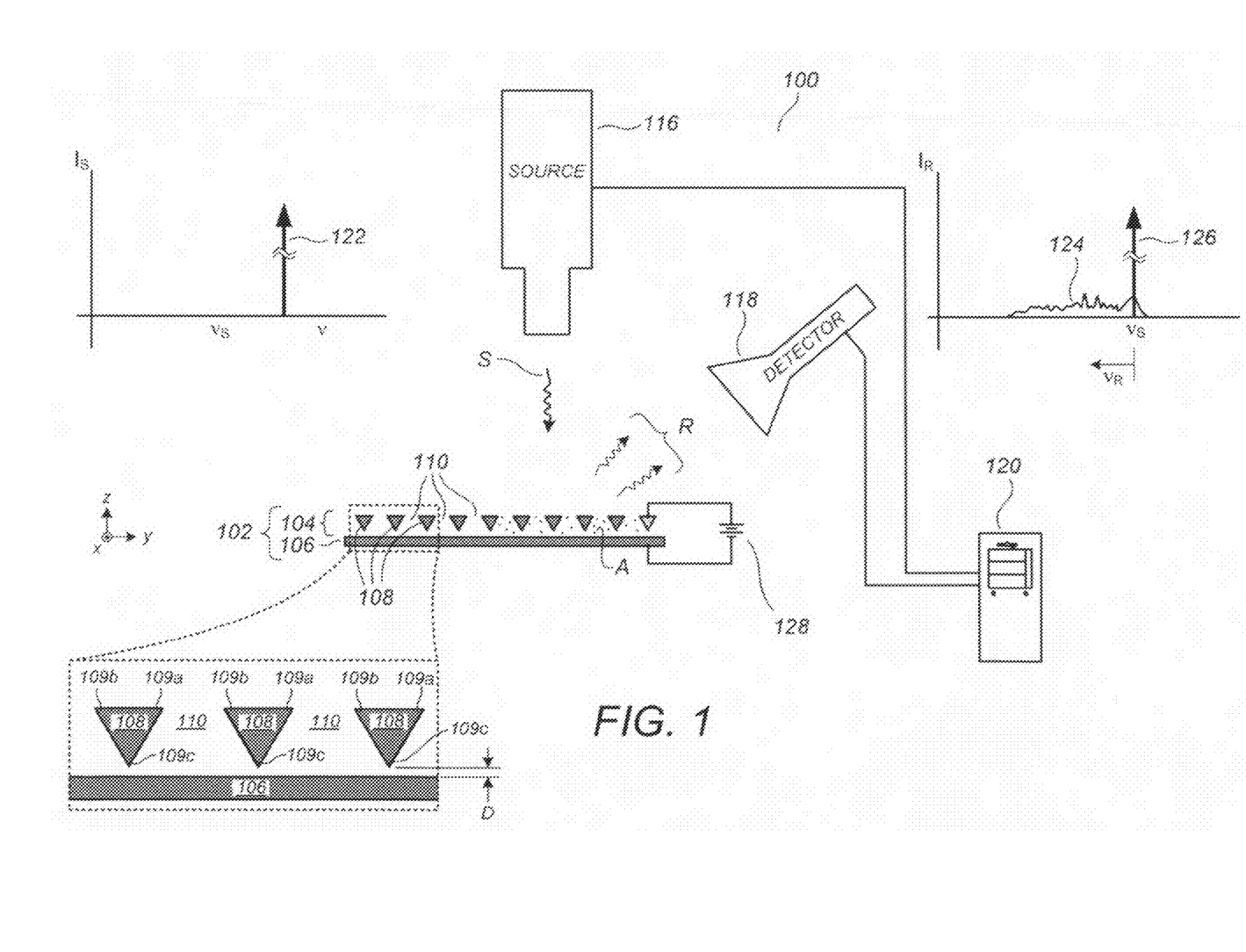
FIG. 1 illustrates an apparatus for facilitating surface-enhanced Raman spectroscopy (SERS) according to an embodiment.

FIG. 1 illustrates an apparatus 100 for facilitating surface-enhanced Raman spectroscopy (SERS) according to an embodiment, which is referenced herein as SERS system 100. SERS system 100 comprises a SERS-active structure 102 near which and/or within which at least one analyte molecule "A" is disposed. The SERS-active structure 102 comprises a metallic fishnet 104 and a metallic platform 106 proximal to the metallic fishnet 104. For clarity of presentation, FIG. 1 illustrates a single relevant cross-section of the metallic fishnet 104 according to an embodiment, the chosen cross-section causing it to appear as a set of separate floating components, but it will be readily understood that the illustrated components are supported by a larger fishnet structure as set forth further infra. As described further infra, in other embodiments the metallic platform 106 may be omitted, wherein the SERS-active structure 102 consists essentially of the metallic fishnet 104.

The analyte molecules "A" may be a gas or part of a gas mixture within which the SERS-active structure 102 is disposed. As another example, the analyte molecules "A" may be contained in a gas or liquid that is directed toward the SERS-active structure 102 by a microfluidic system (not shown). As yet another example, the analyte molecules "A" may be contained in a liquid that is manually dropped onto the SERS-active structure 102 using a dropper. The scope of the present teachings includes, without limitation, any of a variety of different mechanisms operable to cause the analyte molecules "A" to be transported and/or maintained within and/or around the SERS-active structure 102. By way of example and not by way of limitation, for embodiments in which the metallic platform 106 is omitted, a liquid analyte may be maintained along the metallic fishnet 104 simply by surface tension.

SERS system 100 further comprises a radiation source 116 and a detector 118. The radiation source 116 provides a strong monochromatic light beam "S," a monochromatic spectrum 122 thereof being illustrated in FIG. 1 as a plot of intensity versus wavenumber. The light beam "S" typically has a spot size of about 1 μm-5 μm. By way of non-limiting example and not by way of limitation, an exemplary range of wavelengths of incident radiation for which one or more of the embodiments is applicable includes wavelengths between about 400 nm and about 2000 nm.

Radiation "R" that emerges from the analyte molecules "A" and SERS-active structure 102 comprises a reflected and/or Rayleigh component 126 and a Raman component 124. The detector 118 optically filters out the reflected and/or Rayleigh component 126 and detects an intensity of the Raman scattered radiation 124 for each wavelength near the incident wavelength. Typically, a processor 120 controls the radiation source 116 and the detector 118 and receives readings from the detector 118 to produce a Raman spectrum readout, the peaks and valleys of which are then used for analyzing the analyte molecules "A." The Raman spectrum readout is often presented as a plot of intensity versus Raman shift, the Raman shift being defined as the difference $v_R$ between the wavenumbers of the source and Raman-scattered radiation. Peaks and valleys that are meaningful for purposes of chemical analysis are often for Raman shifts in the range of 500 $cm^{-1}$-2000 $cm^{-1}$, which for a typical source wavelength of 1000 nm would correspond to Raman-scattered photons having wavelengths between 1050 nm-1250 nm.

Examples of suitable metals for the metallic fishnet 104 and metallic platform 106 include silver (which is particularly advantageous because of small dissipation), gold, copper, platinum, palladium, titanium, and aluminum, and other metals exhibiting analogous SERS-active characteristics when configured according to one or more of the embodiments. The surfaces of the metallic fishnet 104 and/or metallic platform 106 near which the analyte molecules "A" are disposed are preferably derivatized or functionalized by attachment of receptors or ligands (not shown) that promote the binding of a particular analyte molecule in proximity thereto. The ligand may be repulsive or neutral relative to other molecules. The ligand and the analyte molecule may consist of what is often referred to as a specific pair or a recognition pair of molecules. The particular analyte molecule may include, but is not limited to, biomolecules such as nucleic acids, proteins, hormones, sugars, and metabolites. The ligand may include, but is not limited to, antibodies, receptors, and nucleic acids. Techniques for functionalizing surfaces for attachment of particular analyte molecules thereto have been researched and developed extensively in the art of biosensors and bioassays and can be employed.

In the embodiment of FIG. 1, the radiation source 116 directs the light beam "S" toward a face of the metallic fishnet 104. In other embodiments, the incident radiation can propagate laterally (i.e., in the x-y plane of FIG. 1) toward the analyte molecules "A" using a lateral waveguiding arrangement. Typically, the Raman scattered photons are scattered isotropically from the analyte molecules. For one embodiment, the detector 118 is positioned at an angle that minimizes the intensity of the reflected and/or Rayleigh-scattered radiation incident thereon, such angle being identifiable analytically and/or empirically based on the precise locations and configurations of the source 116 and SERS-active structure 102.

For embodiments in which the incident radiation propagates laterally toward the analyte molecules "A" in a lateral waveguiding arrangement, such as may be useful for "system-on-a-chip" SERS-based devices, a scattered-radiation waveguide may be provided that guides the scattered radiation laterally toward a first radiation detector. In another embodiment (see, for example, FIG. 7, infra), to increase the efficiency of scattered radiation detection, a second radiation detector may be placed above the face of the metallic fishnet 104, optionally accompanied by a lensing system, to capture a greater percentage of the scattered radiation.

Figure 2:
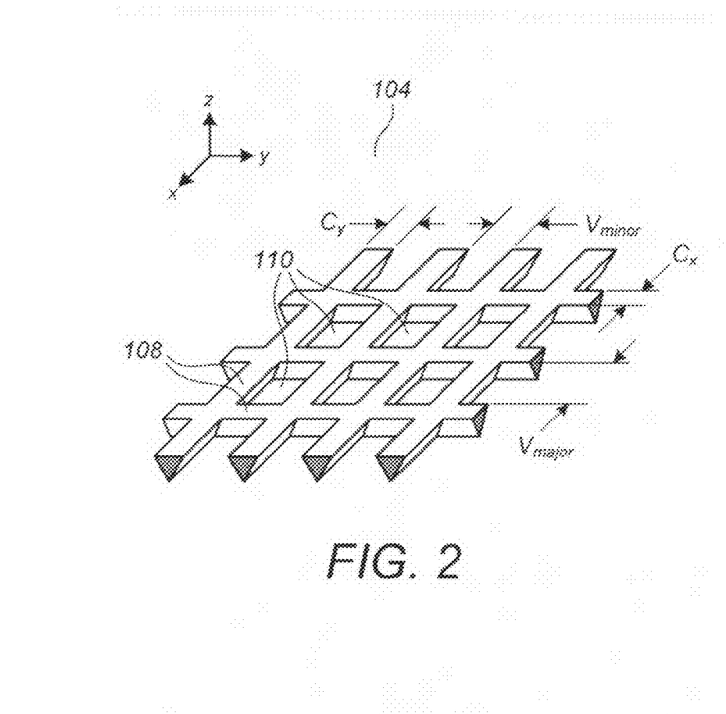
FIG. 2 illustrates a perspective view of a metallic fishnet of the apparatus of FIG. 1.

FIG. 2 illustrates a perspective view of the metallic fishnet 104 of FIG. 1. Referring now to both FIG. 1 and FIG. 2 as necessary, metallic fishnet 104 comprises a plurality of metallic conductors 108 disposed in an interconnected lateral pattern, i.e., in a pattern extending in the x-y plane according to the Cartesian coordinate system shown in FIG. 1 and FIG. 2. The lateral pattern of metallic conductors 108 defines, in turn, a lateral pattern of voids 110 thereamong. The voids 110 comprise a dielectric such as air. Dielectric materials other than air in any form (vacuum, gas, liquid, or solid) may also be used, either alternatively or in conjunction with air, provided that introduction of the analyte molecules "A" near the metallic fishnet 104 can be physically accommodated. More generally, as used herein, metallic fishnet refers to a metallic film or metallic sheet having holes patterned therethrough, it not being required that the metallic conductors 108 be wire-like or bar-like between intersections as in the metallic fishnet of FIGS. 1-2. For example, a metallic fishnet can be formed by a metallic film that has been patterned with circular holes, triangular holes, irregularly shaped holes, etc., without departing from the scope of the present teachings.

According to an embodiment, the metallic fishnet 104 exhibits at least one acute V-shaped cross-sectional feature between at least one adjacent pair of the voids 110. When viewed in cross-section between neighboring ones of the voids 110, the metallic conductor material that forms the metallic fishnet 104 should have an outline that, for at least one location, extends outward into the air (or the surrounding dielectric) in a generally sharp or cornered manner in which a vertex of the generally sharp or cornered feature forms an acute angle, i.e., an angle that is less than 90 degrees. In the example of FIG. 1, the cross-sections between the voids 110 correspond to normal cross-sections of each metallic conductor 108. Examples of acute V-shaped cross-sectional features in FIG. 1 include each of the vertexes 109a, 109b, and 109c, each having a vertex angle less than 90 degrees.

According to another embodiment, a metallic fishnet is provided exhibiting at least one acute V-shaped cross-sectional feature between at least one adjacent pair of its voids that is less than 60 degrees. In yet another embodiment, a metallic fishnet is provided exhibiting at least one acute V-shaped cross-sectional feature between at least one adjacent pair of its voids that is less than 45 degrees. In still another embodiment, a metallic fishnet is provided exhibiting at least one acute V-shaped cross-sectional feature between at least one adjacent pair of its voids that is less than 30 degrees.

The SERS system 100 of FIG. 1 represents one example in which the SERS-active structure 102 includes a metallic platform 106 in close proximity to the metallic fishnet 104, being separated from the vertexes 109c by a distance D that, for one embodiment, is less than one-twentieth of a wavelength of the incident radiation S. For example, for an incident radiation wavelength of 400 nm, the distance D should be less than about 20 nm. In another embodiment, for an incident radiation wavelength of about 1600 nm, the distance D is in the range of 5 nm-10 nm. SERS system 100 further comprises a voltage source 128 coupled to apply a voltage (for example, a DC voltage of about 0.1 volt) between the metallic fishnet 104 and the metallic platform 106, which is advantageous for enhancing electric field intensity near the vertexes 109c for further enhancement of Raman scattered radiation intensity. For embodiments in which the metallic fishnet 104 is used without the metallic platform 106, the voltage source 128 may be omitted.

For a particular source radiation wavelength, the patterning and dimensions for the metallic fishnet 104 will be generally comparable to those required for so-called metamaterial and/or negative index material behavior (i.e., displaying negative effective permittivity, negative effective permeability, or both for radiation at the source radiation wavelength). However, such metamaterial and/or negative index behavior is not required for effective Raman signal enhancement by the SERS-active structure 102. Generally speaking, in designing a particular metallic fishnet suitable for use according to one or more of the embodiments, lateral configurations and dimensions associated with known metamaterial/negative index material dimensions might be useful as a starting point, but the particular configurations and dimensions best for Raman signal enhancement may vary substantially therefrom. Generally speaking, the design process involves computer simulation and some degree of iteration to arrive at configurations suitable for effective Raman signal enhancement according to one or more of the embodiments. It is to be appreciated that a person skilled in the art would be able to realize a SERS-active structure according to one or more of the embodiments using known simulation platforms, materials, etc., in view of the present disclosure without undue experimentation.

With reference to FIG. 2, the metallic fishnet 104 is characterized by a lateral pattern of the metallic conductors 108 which, in turn, define a lateral pattern of voids 110 thereamong. When viewed from above, the voids 110 have a major dimension $V_{major}$ and a minor dimension $V_{minor}$. It is to be appreciated that although the metallic fishnet 104 of FIGS. 1-2 has rectangular voids, the scope of the embodiments is not so limited. The voids 110 may have any of a variety of regular (e.g., triangular, circular, square, pentagonal, hexagonal, etc.) or irregular shapes without departing from the scope of the present teachings, each characterized by a major dimension and a minor dimension. The major dimension $V_{major}$ and a minor dimension $V_{minor}$ may be the same, or may be different, depending on the particular configuration. According to an embodiment, the minor lateral dimension $V_{minor}$ is less than the incident radiation wavelength. The metallic conductors 108 may have the same or different thicknesses in different directions. According to an embodiment, adjacent ones of the voids 110 are laterally separated by a distance that is less than the incident radiation wavelength. Thus, for the example of FIG. 2, the conductor dimensions $C_x$ and $C_y$ are each preferably less than the incident radiation wavelength.

As used herein, the term SERS also encompasses the term NERS (nano-enhanced Raman spectroscopy) and, accordingly, the SERS-active structure 102 may alternatively be referenced as a NERS-active structure. The SERS-active structure 102 provides extraordinary (many orders of magnitude) enhancement of the intensity of Raman radiation that would otherwise be emitted by the analyte molecules "A". Moreover, the SERS-active structure 102 can provide substantial improvement, perhaps even by a factor up to $10^6$, over other SERS-active structures such as nano-roughened metal surfaces.

The relative importance of the various mechanisms that may fully or partially underlie the SERS enhancement phenomenon are, arguably, still open to debate in the scientific community. From a purely electromagnetic perspective (neglecting effects related to renormalization of molecule oscillator strength due to binding, reconfiguration of electronic states, and other possibly strong and non-universal factors of chemical origin), approaches based on linear Raman response have been formulated for characterizing the enhancement factor $f^R$. The electromagnetic (EM) SERS enhancement factor for a molecule bound at a position $r_m$ can be expressed in terms of local field $E_m$ (at the position $r_m$ of the molecule) as $f^R=(E_m/E_0)^4$, where $E_0$ is the field intensity in the incident radiation beam. The fourth power is the result of $f^R$ being a product of the excitation rate enhanced by $\sim I=(E_m/E_0)^2$ and yet another similar factor describing the enhancement of the Raman radiation due to the nanosystem (local environment) working as a resonant transmitting "nano-antenna". A SERS-active structure according to one or more of the embodiments serves to increase/optimize the local environmental EM effect (e.g., increasing the local field). A SERS-active structure according to one or more of the embodiments also serves to support very intense collective plasmon modes (CPM) with strong enhancement of the electric field.

Local field enhancement occurs in resonant EM structures with a large quality factor Q. Therefore, it is advantageous to provide (i) Raman active structures that have a large Q-factor and are suitable for binding molecules, and (ii) structures that couple the incident light effectively into those resonances (i.e., exhibit a light harvesting and/or antenna effect). For these reasons, noble metals are a good choice, and/or heterostructures combining the metal and dielectrics and/or semiconductors. In metals, EM modes tend to be trapped near their interface with vacuum (dielectric or semiconductor), as metals are characterized by a large negative real part of the dielectric constant ($\in_\omega=\in_d-\omega_p^2/\omega[\omega+i\Gamma]$), and are referenced as surface plasmon (SP) modes at $\omega=\omega_n\sim1$ to 10 eV, at which values $Q\sim\omega_n/\gamma$ gets relatively large (~100-1000), limited by ohmic losses ($\gamma\sim0.01$ eV). Semiconductors/dielectrics are suitable for the patterned substrates supporting the metals in that their Q factor may be very large since dielectric losses are so small. A SERS-active structure according to one or more of the embodiments serves to optimize substrates with respect to a combination of light harvesting ability, quality of the resonances, and analyte binding. By way of example, with regard to analyte binding, a high electric field associated with an acute V-shaped cross-sectional feature advantageously tends to attract analytes theretoward (for cases in which the analytes are mobile, as in a gas or non-viscous liquid) by electrostatic force. A SERS-active structure according to one or more of the embodiments exhibits an advantageously high degree of coupling of the incident radiation into local EM resonance modes (SP modes).

Figure 3A:
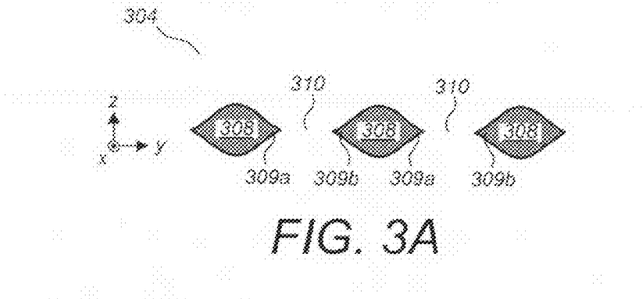
FIGS. 3A-3C illustrate examples of cross-sectional shapes of metallic fishnets according to one or more of the embodiments.
Figure 3B:
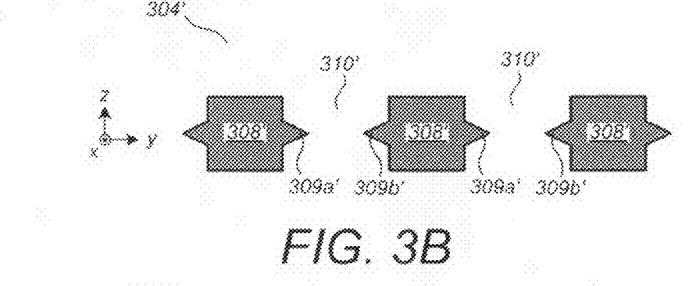
Figure 3C:
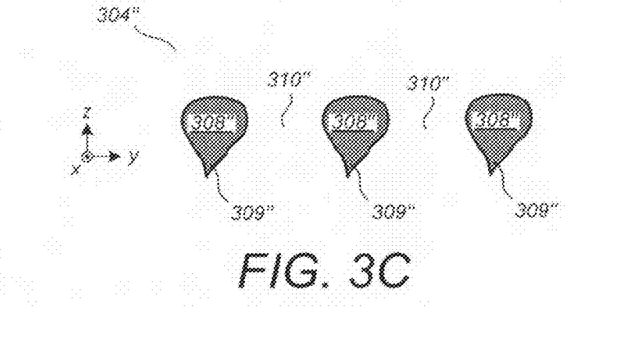

FIGS. 3A-3C illustrate examples of cross-sectional shapes of metallic fishnets for SERS enhancement and/or use in a SERS-active structure according to one or more of the embodiments. FIG. 3A illustrates cross-sections of metallic conductors 308 of a metallic fishnet 304 according to an embodiment, the metallic conductors 308 separating respectively adjacent pairs of voids 310. For a rectangular lateral pattern (when viewed from above) similar to that of FIG. 2, the voids 310 each have first and second opposing sides, and the metallic fishnet 304 exhibits an acute V-shaped cross-sectional feature (309a, 309b) for each of the opposing sides. Each of the acute V-shaped cross-sectional features (309a, 309b) points toward the other of the first and second sides. This is also the case for the acute V-shaped cross-sectional features 309a' and 309b' of FIG. 3B, which illustrates cross-sections of metallic conductors 308' of a metallic fishnet 304' according to an embodiment, the metallic conductors 308' separating respectively adjacent pairs of voids 310'. FIG. 3C illustrates cross-sections of metallic conductors 308" of a metallic fishnet 304" according to an embodiment, the metallic conductors 308" separating respectively adjacent pairs of voids 310". As illustrated further hereinbelow (see FIG. 9, infra), surface plasmon resonance effects and the associated intensified electric fields sufficient for improved Raman signal amplification can be achieved even where there is only a single acute V-shaped cross-sectional feature, such as the vertex 309", between each pair of adjacent voids 310".

Figure 4:
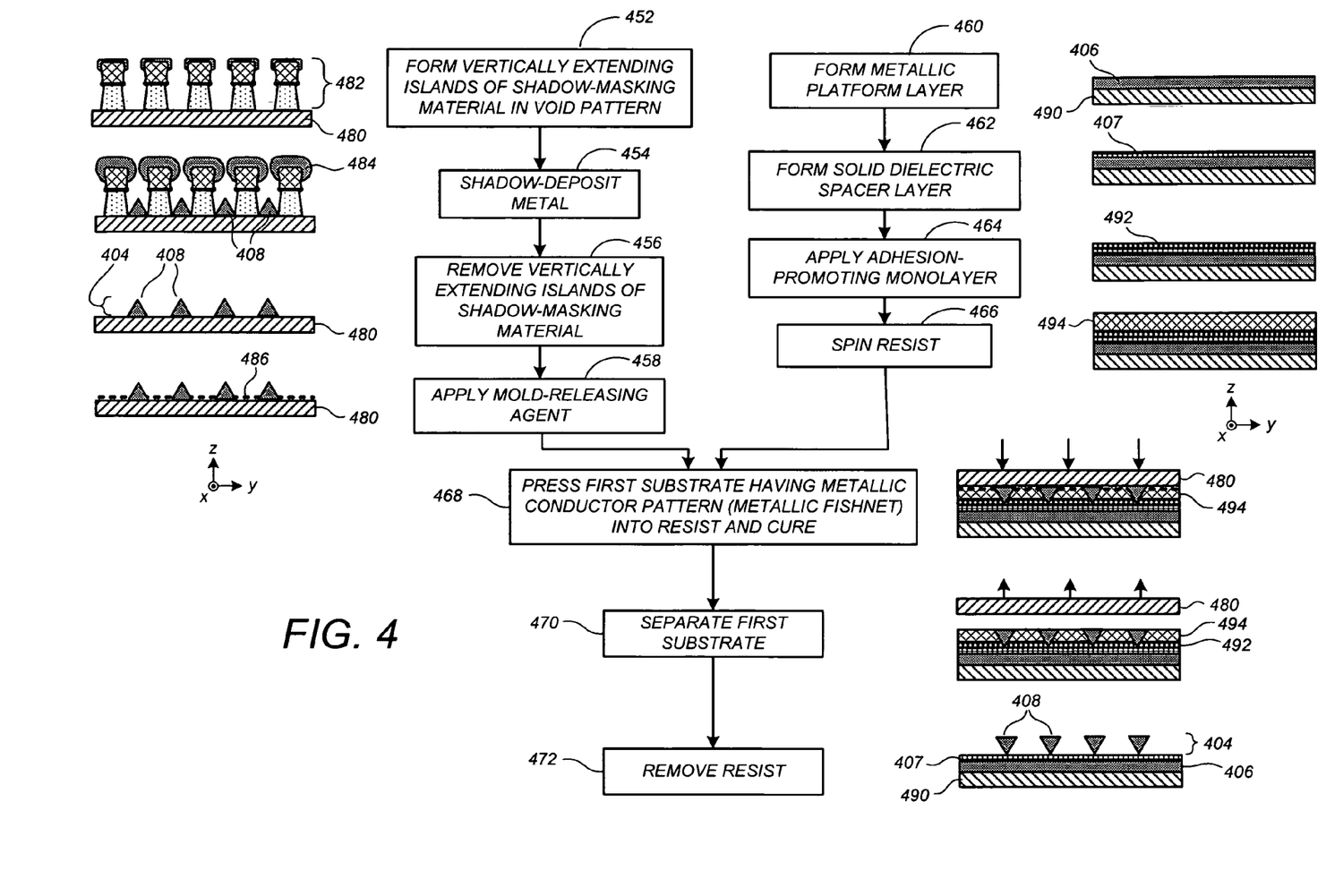
FIG. 4 illustrates fabricating a SERS-active structure according to an embodiment.

FIG. 4 illustrates fabricating a SERS-active structure according to an embodiment, and includes conceptual side cut-away views of the structure as it is being fabricated next to each of the text boxes. Steps 452-458 are directed generally to fabricating a metallic fishnet 404 that is similar to the metallic fishnet 104 of FIGS. 1-2. The metallic fishnet 404 is characterized by a predetermined lateral metallic conductor pattern. The predetermined lateral metallic conductor inherently defines, of course, a corresponding predetermined lateral void pattern, and vice versa, because each is the spatial inverse of the other.

At step 452, a plurality of vertically extending islands 482 of shadow-masking material are laterally patterned onto a substrate 480 according to the desired predetermined lateral void pattern. The substrate 480 can be glass, quartz, silicon, or any of a variety of similarly suitable materials. Any of a variety of shadow masking materials, including various layered combinations of materials suitable for shadow masking, can be used and would be known to a person skilled in the art, and therefore the stacked materials of the vertically extending islands 482 are not individually numbered in FIG. 4. In one example, these materials can include a 200 nm thick cross-linked polymer bottom, a 20 nm thick dielectric ($SiO_2$) middle layer, and a 200 nm thick upper layer of imprint resist, the stacks being laterally patterned by nanoimprint lithography and reactive ion etching.

At step 454, a metal (e.g., silver) is shadow-deposited to form a lateral pattern of metallic conductors 408 according to the predetermined lateral conductor pattern. The vertically extending islands 482 are configured and dimensioned such that each of the shadow-deposited metallic conductors exhibits at least one acute V-shaped cross-sectional feature, which extends upwardly in this example. At step 456, the vertically extending islands 482 of shadow-masking material are removed from the substrate 480, e.g., by wet etching, resulting in a metallic fishnet 404 comprising the metallic conductors 408 disposed on the substrate 480. At step 458, a mold releasing agent 486 is applied to the substrate 480 that is non-adhesive to the shadow-deposited metallic conductors 408 to allow subsequent separation from a cured resist layer.

At step 460, a metallic platform 406 comprising silver, for example, is deposited on a substrate 490, which can be similar or dissimilar in material selection to the substrate 480. At step 462, a solid dielectric spacer layer 407, comprising silicon oxide ($SiO_x$), for example, is formed on the metallic platform 406, wherein the spacer layer 407 has a thickness corresponding to a predetermined separation distance between the acute V-shaped cross-sectional features and the metallic platform 406 (see FIG. 1, distance "D", supra). At step 464, an adhesion-promoting monolayer 492 comprising, for example, hexamethyldisilazane (HDMS), is applied to the spacer layer 407 to promote adhesion to a UV resist layer 494 which is spun thereon at step 466.

At step 468, the substrate 480 containing the upwardly facing metallic fishnet 404 is turned upside down and compressed against the UV resist layer 494 until the acute V-shaped cross-sectional features achieve mechanical contact with the spacer layer 407, and the UV resist is cured. At step 470, the substrate 480 is separated, and at step 472, the UV resist is removed, whereby the shadow-deposited metallic conductors 408 remain supported by the dielectric spacer layer 407 above the metallic platform 406. The resultant assembly is similar to the SERS-active structure 102 of FIG.

1 except for the presence of the dielectric spacer layer 407, whose electromagnetic impact can be accounted for in the initial device design. The resultant assembly is advantageous in its structural stability, but is less advantageous than other embodiments herein in terms of microfluidic accommodation due to the presence of the dielectric spacer layer 407.

Figure 5:
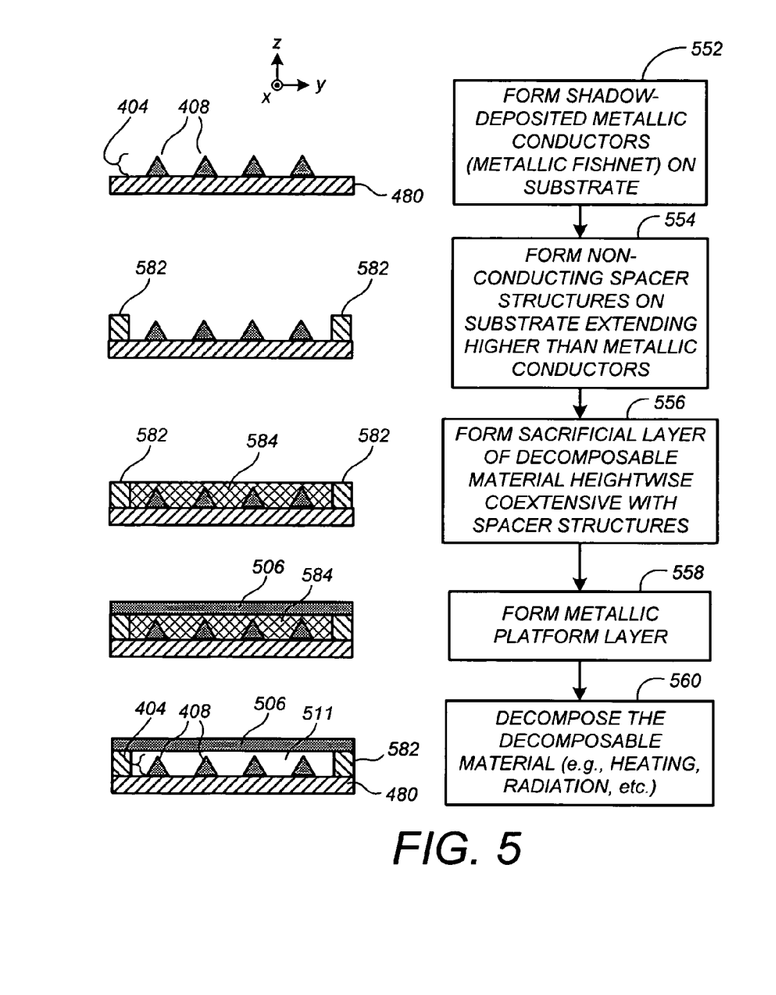
FIG. 5 illustrates fabricating a SERS-active structure according to an embodiment.

FIG. 5 illustrates fabricating a SERS-active structure according to an embodiment. At step 552, the upward-facing metallic fishnet 404 comprising metallic conductors 408 disposed on the substrate 480 is formed using the steps 454-456 of the method of FIG. 4, supra. For applications in which the analyte is to receive source radiation from above the surface of the SERS-active structure, as in the embodiment of FIG. 1, the substrate 480 should be substantially transparent at the source radiation wavelength and wavelengths therearound. For applications in which the analyte is to receive source radiation propagating parallel to the surface of the SERS-active structure (for example, in integrated "system-on-a-chip" applications, see FIG. 7, infra), it is not required that the substrate 480 be transparent at the source radiation wavelength. The metallic conductors 408 rise upward above the substrate 480 by a first height.

At step 554, a plurality of non-conducting spacer structures 582 are formed that extend upward from the substrate 480 by a second height extending beyond the first height of the metallic conductors 408 by an intended separation distance (see FIG. 1, distance "D"). The spacer structures 582, which can be fabricated using known methods using any of a variety of different nonconducting materials, can optionally be used as microfluidic guides and/or channels for sample introduction and expulsion. Accordingly, the spacer structures 582 can be post-type structures, wall-type structures, or combinations thereof as needed. At step 556, a sacrificial layer of decomposable material 584 is formed on the substrate 480 and above the metallic conductors 408, extending laterally between the spacer structures 582 and extending upwardly from the substrate 480 to be heightwise coextensive with the spacer structures 582. Examples of decomposable materials include decomposable polymers such as polynorbornene and polycarbonate, which can be chemically and/or thermally decomposed. At step 558, a metallic platform layer 506 is formed atop the spacer structures 582 and the sacrificial layer of decomposable material 584. At step 560, the sacrificial layer of decomposable material 584 is decomposed, leaving an empty channel 511, and leaving the metallic platform 506 supported by the spacer structures 582.

Figure 6:
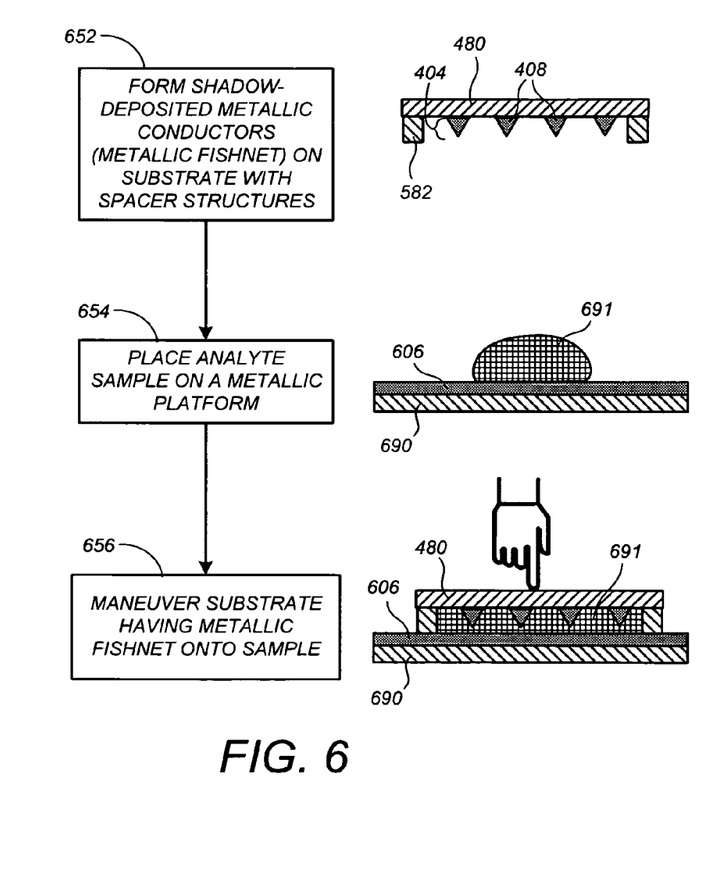
FIG. 6 illustrates fabricating a SERS-active structure according to an embodiment.

FIG. 6 illustrates fabricating a SERS-active structure according to an embodiment, wherein the SERS-active structure is assembled in "real time" during field application of the overall SERS-based device. At step 652, the metallic fishnet 404 comprising metallic conductors 408 disposed on the substrate 480 is formed using the steps 454-456 of the method of FIG. 4, supra, and spacer structures formed thereon according to step 554 of the method of FIG. 5, supra. At step 654, a fluidic sample 691 including at least one analyte molecule is placed on a metallic platform 606. At step 656, the substrate 480 with metallic fishnet 404 and spacer structures 582 is manually or robotically maneuvered into contact with the fluidic sample 691, the metallic conductors 408 facing the metallic platform 606, until the spacer structures 582 abut the metallic platform 606. For applications in which the analyte is to receive source radiation from above the surface of the resultant SERS-active structure, as in the embodiment of FIG. 1, the substrate 480 should be substantially transparent at the source radiation wavelength and wavelengths therearound. For applications in which the analyte is to receive source radiation propagating parallel to the surface of the SERS-active structure (for example, in integrated "system-on-a-chip" applications, see FIG. 7, infra), it is not required that the substrate 480 be transparent at the source radiation wavelength.

Figure 7:
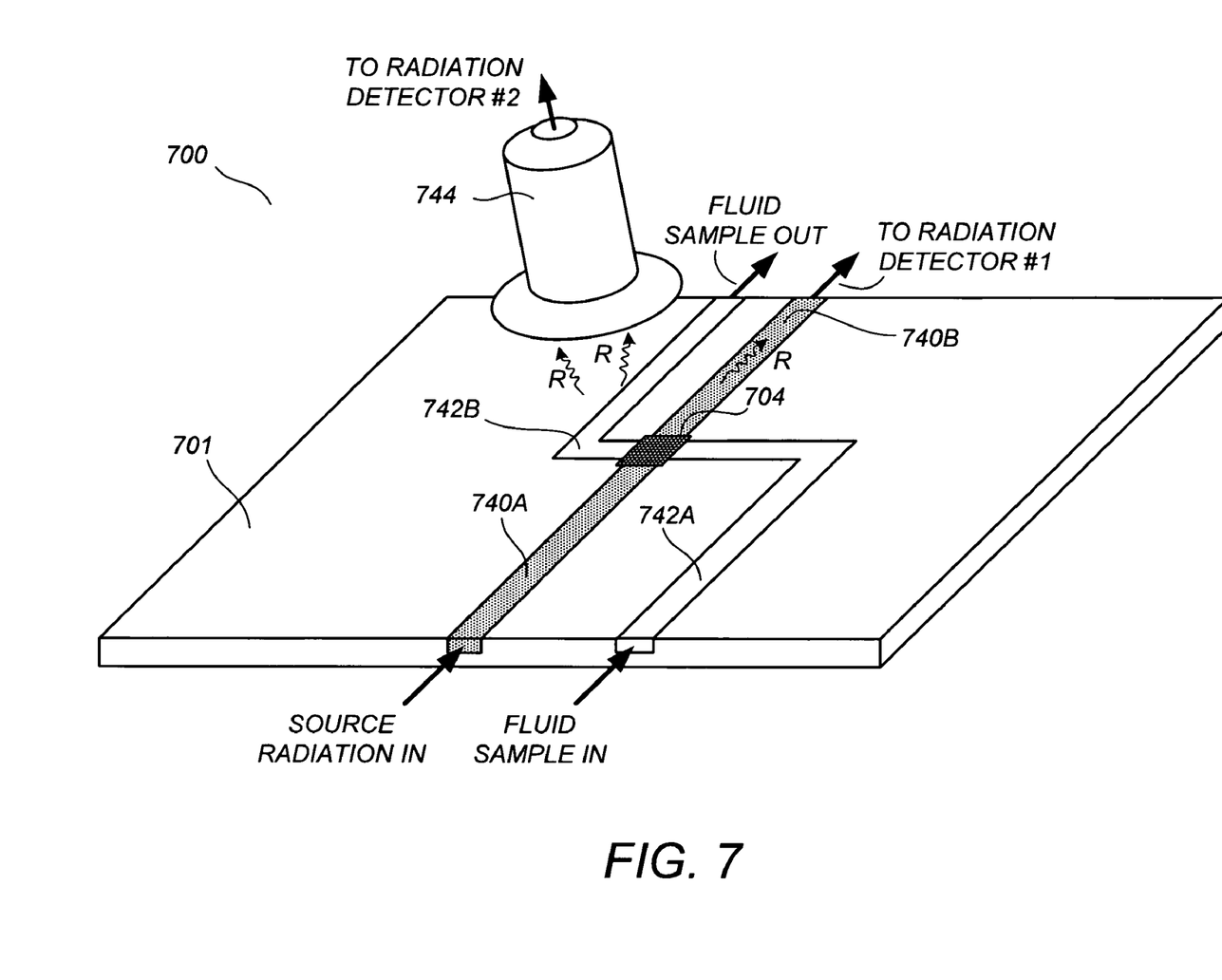
FIG. 7 illustrates a perspective view of an apparatus for facilitating SERS according to an embodiment.

FIG. 7 illustrates a perspective view of an apparatus 700 for facilitating SERS according to an embodiment, which in one embodiment can be used as part of an integrated or "system-on-a-chip" SERS configuration. The apparatus 700 comprises a metallic fishnet 704 (optionally with a metallic platform thereunderneath) disposed on a substantially planar integrated circuit device 701, which can be a monolithic chip or a collection of chip devices. The apparatus 700 further comprises a microfluidic system including channels 742A and 742B for guiding fluid toward and away from the metallic fishnet 704, respectively. The apparatus 700 further comprises an incident radiation waveguide 740A laterally guiding incident radiation toward the metallic fishnet 704 and the analyte molecule placed therenear by the microfluidic system. The apparatus 700 further comprises a first radiation detector configured to receive radiation scattered from the analyte molecule(s) and collected by virtue of an output waveguide 740B. Because Raman scattering is generally an isotropic process, it may be necessary to capture more scattered radiation than can be collected into the output waveguide 740B. Accordingly, for another embodiment, a lensing system 744 is placed above of the plane of the metallic fishnet 704 to guide scattered radiation to a second radiation detector.

Figure 8A:
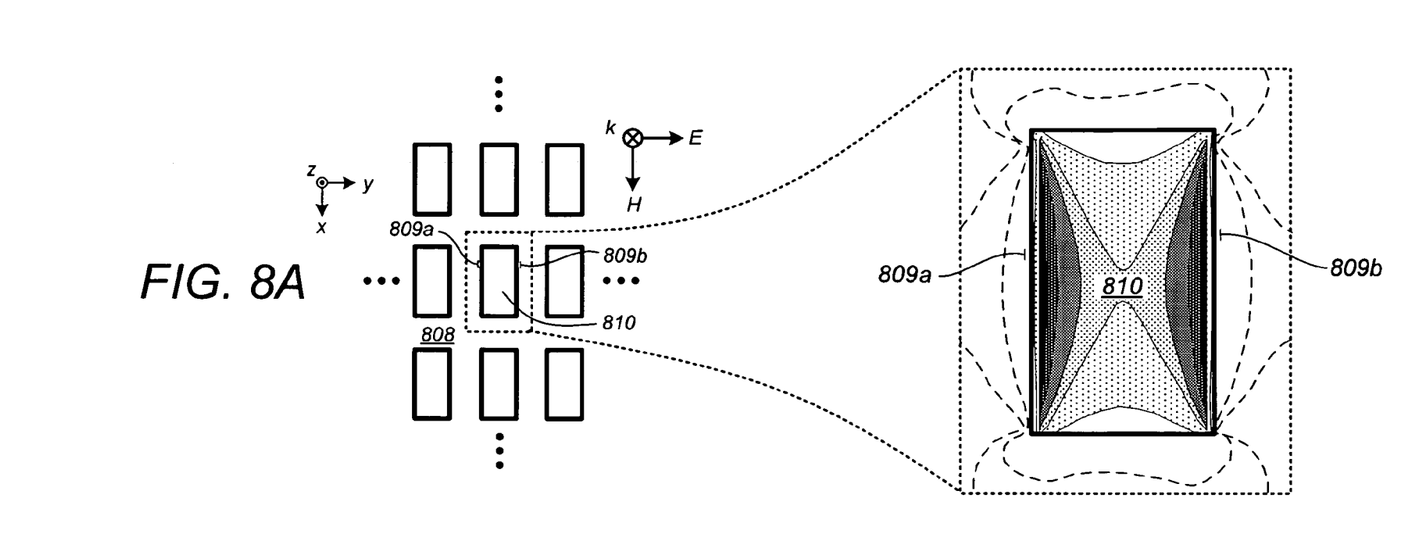
FIG. 8A illustrates a top view of a SERS-active structure according to an embodiment and a corresponding electric field intensity map.
Figure 8B:
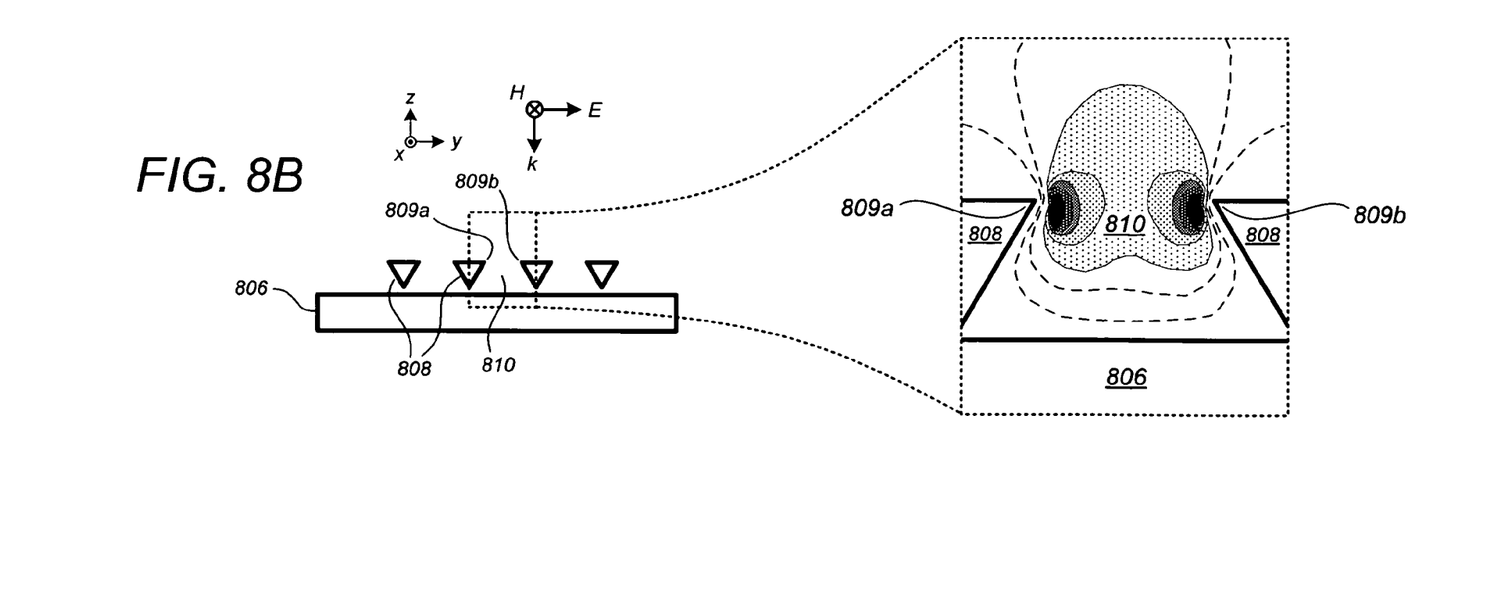

FIG. 8A illustrates a top view of a SERS-active structure according to an embodiment and a corresponding electric field intensity map generated by computer simulation. FIG. 8B illustrates a side view of the SERS-active structure of FIG. 8A and a corresponding electric field map. The SERS-active structure of FIG. 8 is similar to that of FIG. 1, supra, except that no external DC voltage is supplied between its metallic conductors 808 and a nearby metallic platform 806. An enlarged view of a representative void 810 is shown, with darkly shaded areas corresponding to very strong EM field, lighter areas corresponding to less intense EM fields, and dotted lines corresponding to substantially weaker EM fields.

For the computer simulation, polarized source radiation was applied having a wavelength of 900 nm and being normally incident in the −z direction (k-vector in the −z direction), with the electric field pointing in the y-direction. The metallic conductors 808 formed equilateral triangles in cross-section that were 300 nm on a side with bottom vertexes separated from the metallic platform 806 by 5 nm. The voids 810 were rectangular with a dimension of 300 nm in the y-direction and 600 nm in the x-direction. As illustrated in FIGS. 8A-8B, very strong EM fields were observed along the facing vertexes 809a and 809b pointing toward each other and pointing in the direction of the electric field. In operation, the analyte molecule(s) close to the vertexes 809a and 809b will exhibit very strong Raman signal intensification.

Figure 9:
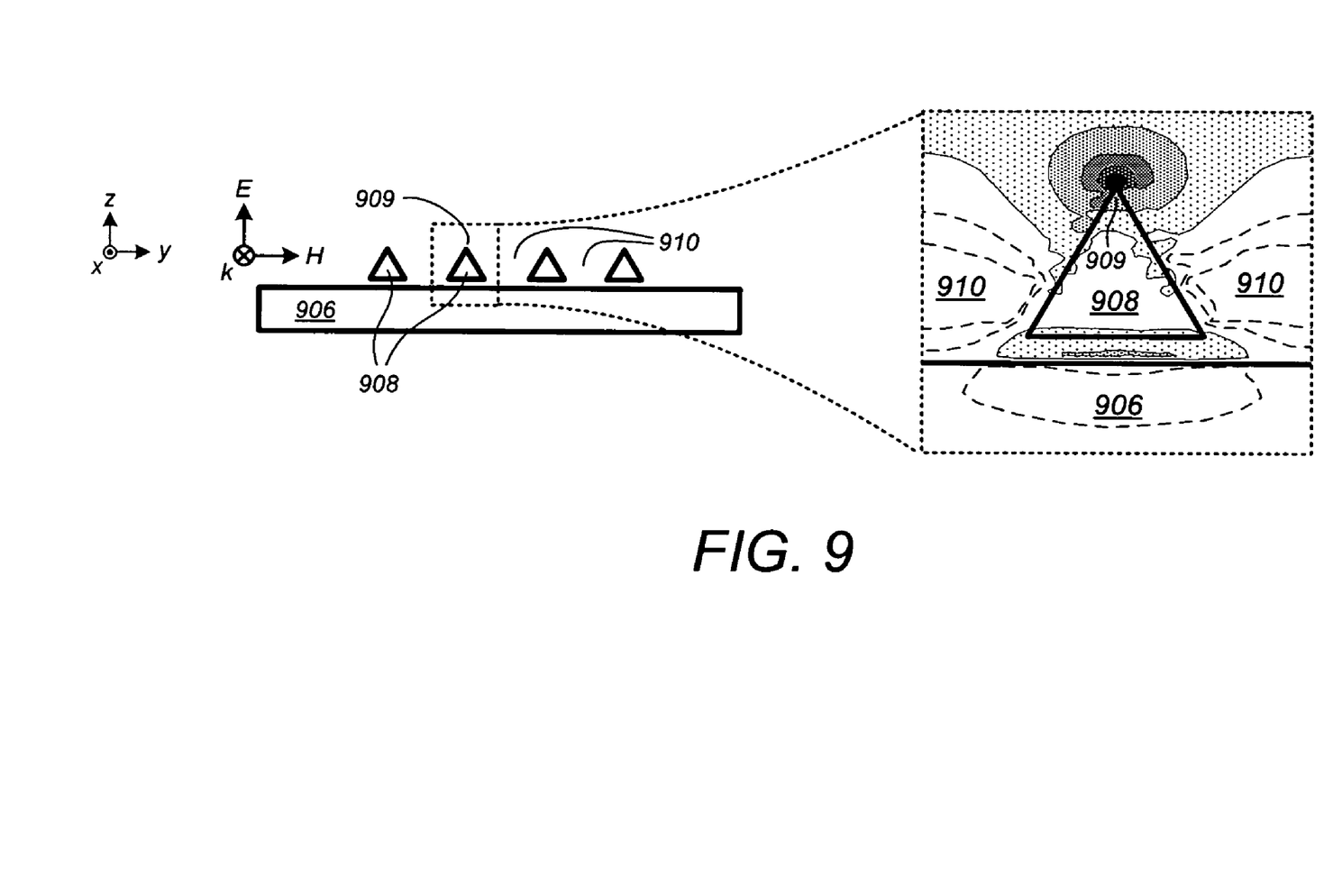
FIG. 9 illustrates a side view of a SERS-active structure according to an embodiment and a corresponding electric field map.

FIG. 9 illustrates a side view of a SERS-active structure according to an embodiment and a corresponding electric field map generated by computer simulation. For the computer simulation, polarized source radiation was applied having a wavelength of 800 nm and propagating parallel to the surface of the SERS-active structure, as may be applied in "system-on-a-chip" applications. In particular, the source radiation propagated in the −x direction (k-vector in the −x direction), with the electric field pointing upward in the z-direction. The lateral footprint and dimensions of the metallic conductors 908 was similar to those of FIG. 8, supra, except that the cross-sectional shape was inverted relative to the metallic platform 906 as shown, and the flat bottom surface of the metallic conductors 908 was separated from the metallic platform 906 by 50 nm. As illustrated in FIG. 9, very strong EM fields were observed along the upwardly pointing vertex 909. In operation, the analyte molecule(s) close to the vertex 909 will exhibit very strong Raman signal intensification. A weaker but still significant EM field (about 25% of the peak intensity near the vertex 909) was also observed in the 50 nm gap between the bottom surface of the metallic conductors 908 and the metallic platform 906, so analyte molecules near that region will also exhibit strong Raman signal intensification In view of the disclosure hereinabove, fabrication of devices according to one or more of the embodiments can be achieved using known integrated circuit fabrication methods including, but not limited to: deposition methods such as chemical vapor deposition (CVD), metal-organic CVD (MOCVD), plasma enhanced CVD (PECVD), chemical solution deposition (CSD), sol-gel based CSD, metal-organic decomposition (MOD), Langmuir-Blodgett (LB) techniques, thermal evaporation/molecular beam epitaxy (MBE), sputtering (DC, magnetron, RF), and pulsed laser deposition (PLD); lithographic methods such as optical lithography, extreme ultraviolet (EUV) lithography, x-ray lithography, electron beam lithography, focused ion beam (FIB) lithography, and nanoimprint lithography; removal methods such as wet etching (isotropic, anisotropic), dry etching, reactive ion etching (RIE), ion beam etching (IBE), reactive IBE (RIBE), chemical-assisted IBE (CAIBE), and chemical-mechanical polishing (CMP); modifying methods such as radiative treatment, thermal annealing, ion beam treatment, and mechanical modification; and assembly methods such as stacking, wafer bonding, surface mount, and other wiring and bonding methods.

Whereas many alterations and modifications of the embodiments will no doubt become apparent to a person of ordinary skill in the art after having read the foregoing description, it is to be understood that the particular embodiments shown and described by way of illustration are in no way intended to be considered limiting. By way of example, the present teachings can be used with hyper Raman spectroscopy in which higher order harmonics of the source radiation are considered. By way of further example, multiple similar or different SERS-active substrate structures (e.g., having variations, chirps, etc. in the lateral void patterns of their metallic fishnets) can be arrayed together for use in conjunction with a single laser source or multiple laser sources to promote any of a variety of improved characteristics including, but not limited to, portability, dependability, reusability, cost efficiency, calibration reliability, and/or adaptability for differing analyte molecule types, without departing from the scope of the present teachings. Thus, reference to the details of the described embodiments are not intended to limit their scope.

What is claimed is:

1. An apparatus for facilitating surface-enhanced Raman spectroscopy (SERS) comprising a metallic fishnet defining a plurality of voids therein, wherein said metallic fishnet exhibits at least one acute V-shaped cross-sectional feature between at least one adjacent pair of said voids, said apparatus for facilitating SERS-based sensing in which incident radiation is directed toward at least one analyte molecule disposed near said metallic fishnet, each of said voids having a major lateral dimension and a minor lateral dimension relative to a laterally extending face of the metallic fishnet, wherein said minor lateral dimension is less than a wavelength of the incident radiation, and wherein adjacent ones of said voids are laterally separated by a distance that is less than said wavelength.

2. The apparatus of claim 1, each of said voids having first and second opposing sides, wherein said metallic fishnet exhibits an acute V-shaped cross-sectional feature for each of said opposing sides, each of said acute V-shaped cross-sectional features pointing toward the other of said first and second sides.

3. The apparatus of claim 2, wherein, for each of said voids, said first and second opposing sides are parallel to each other relative to the laterally extending face of the metallic fishnet, and wherein said first and second opposing sides define said minor lateral dimension of said void.

4. The apparatus of claim 3, wherein said metallic fishnet exhibits a triangular cross-sectional shape between each adjacent pair of said voids, said triangular cross-sectional shape defining three acute V-shaped cross-sectional features.

5. The apparatus of claim 1, said laterally extending face of said metallic fishnet being substantially planar, the apparatus further comprising a substantially planar metallic platform positioned substantially parallel to and in non-touching proximity with said laterally extending face.

6. The apparatus of claim 5, said metallic fishnet exhibiting a plurality of acute V-shaped cross-sectional features across a respective plurality of adjacent pairs of said voids, each of said acute V-shaped cross-sectional features pointing outward from said laterally extending face toward said metallic platform and being separated therefrom by a common predetermined distance, the apparatus further comprising an electrical voltage source applying an electrical voltage between said metallic fishnet and said metallic platform.

7. The apparatus of claim 6, wherein said wavelength lies between 400 nm and 2000 nm, and wherein said common predetermined distance is less than about 20 nm.

8. The apparatus of claim 1, said metallic fishnet exhibiting a plurality of acute V-shaped cross-sectional features across a respective plurality of adjacent pairs of said voids, further comprising:
   a radiation source positioned to direct the incident radiation toward the at least one analyte molecule disposed near the metallic fishnet; and
   a radiation detector positioned to receive radiation scattered from the at least one analyte molecule.

9. The apparatus of claim 1, further comprising:
   an integrated circuit device having a substantially planar surface, said metallic fishnet being positioned substantially parallel to said surface;
   a microfluidic system formed along said surface configured to direct a fluid including said at least one analyte molecule in close proximity with said metallic fishnet;
   an incident radiation waveguide laterally guiding said incident radiation along said surface toward the metallic fishnet and the at least one analyte molecule; and
   a radiation detector configured to receive radiation scattered from said at least one analyte molecule and collected by at least one of (i) an output waveguide extending along said surface and receiving radiation scattered thereinto, and (ii) a lensing element positioned to receive radiation scattered out of plane relative to said surface.

10. A method for fabricating a SERS-active structure, comprising forming a metallic fishnet having a predetermined lateral metallic conductor pattern that defines a corresponding predetermined lateral void pattern, wherein said forming a metallic fishnet comprises:
   forming a plurality of vertically extending islands of shadow-masking material laterally patterned on a substrate according to the predetermined lateral void pattern;

shadow-depositing a metal on the substrate to form a plurality of metallic conductors thereon according to the predetermined lateral metallic conductor pattern, wherein said vertically extending islands of shadow-masking material are configured and dimensioned such that each of said shadow-deposited metallic conductors exhibits at least one acute V-shaped cross-sectional feature; and causing each of said acute V-shaped cross-sectional features to be in close non-touching proximity to a common laterally extending metallic platform;

said SERS-active structure for use in a SERS-based system having an incident radiation wavelength, wherein each of said voids has a major lateral dimension that is less than said wavelength, wherein each of said metallic conductors has a thickness that is less than said wavelength, wherein said acute V-shaped cross-sectional features extend outward from said substrate by a common first height, wherein said acute V-shaped cross-sectional features and said metallic platform are brought to a mutual predetermined separation distance, and wherein said predetermined separation distance is less than one-twentieth of said wavelength.

11. The method of claim 10, said substrate being a first substrate, the method further comprising:

removing the vertically extending islands of shadow-masking material from said first substrate;

forming said metallic platform by depositing a metallic layer on a second substrate;

forming a solid dielectric spacer layer above said metallic layer, said solid dielectric spacer layer having a thickness corresponding to said predetermined separation distance;

forming an imprint resist layer above said solid dielectric spacer layer;

compressing said first substrate containing said shadow-deposited metallic conductors downward toward said second substrate, said acute V-shaped cross-sectional features being compressed downward into said imprint resist until achieving mechanical contact with said solid dielectric spacer layer.

12. The method of claim 11, further comprising:

prior to said compressing, applying a mold releasing agent to said first substrate that is non-adhesive to the shadow-deposited metallic conductors thereon; and subsequent to said compressing, curing said imprint resist layer, separating said first substrate from the cured imprint resist and from the shadow-deposited metallic conductors, and removing the cured imprint resist, whereby said shadow-deposited metallic conductors remain supported by said solid dielectric spacer layer above said metallic platform.

13. The method of claim 10, further comprising:

removing the vertically extending islands of shadow-masking material from said substrate;

forming a plurality of non-conducting spacer structures extending outward from said substrate by a common second height extending beyond said first height by said predetermined separation distance;

forming a sacrificial layer of decomposable material on said substrate extending laterally between said spacer structures and extending outwardly from said substrate by said common second height of said spacer structures;

forming said metallic platform by depositing a metallic layer across said decomposable material and said spacer structures; and decomposing said decomposable material of said sacrificial layer, whereby said metallic platform remains supported by said spacer structures and separated from said acute V-shaped cross-sectional features by said predetermined separation distance.

14. The method of claim 10, wherein said causing said acute V-shaped cross-sectional features to be in close non-touching proximity to said metallic platform is performed in real time during a use of said SERS-based system, the method further comprising:

removing the vertically extending islands of shadow-masking material from said substrate;

forming a plurality of non-conducting spacer structures extending outward from said substrate by a common second height extending beyond said first height by said predetermined separation distance;

placing a fluidic sample including at least one analyte molecule on said metallic platform; and maneuvering said substrate into contact with said fluidic sample, said shadow-deposited metallic conductors and said spacer structures facing said metallic platform, said maneuvering continuing until said spacer structures abut said metallic platform.

15. A method for surface-enhanced Raman spectroscopy (SERS), comprising:

causing at least one analyte molecule to be disposed near a metallic fishnet, the metallic fishnet defining a plurality of voids therein and exhibiting at least one acute V-shaped cross-sectional feature between at least one adjacent pair of the voids;

causing incident electromagnetic radiation to impinge upon the at least one analyte molecule disposed near the metallic fishnet; and causing Raman radiation scattered from the at least one analyte molecule to be detected, said metallic fishnet exhibiting a plurality of acute V-shaped cross-sectional features across a respective plurality of adjacent pairs of said voids, each of said acute V-shaped cross-sectional features pointing outward from said metallic fishnet and separated from a common substantially planar metallic platform by a common predetermined distance, wherein said common predetermined distance is less than about one-twentieth of a wavelength of the incident electromagnetic radiation.

16. The method of claim 15, further comprising causing an electrical voltage to be applied between said metallic fishnet and said metallic platform.

* * * * *